United States Patent [19]

DiGeronimo

[11] 4,375,218

[45] Mar. 1, 1983

[54] FORCEPS, SCALPEL AND BLOOD COAGULATING SURGICAL INSTRUMENT

[76] Inventor: Ernest M. DiGeronimo, 1060 NE. 120th St., Miami, Fla. 33161

[21] Appl. No.: 266,847

[22] Filed: May 26, 1981

[51] Int. Cl.³ .............................................. A61B 17/39
[52] U.S. Cl. ................................ 128/303.17; 128/305; 128/321; 128/354
[58] Field of Search .......... 128/303.1, 303.13, 303.17, 128/305, 321, 322, 354; 81/43

[56] References Cited

U.S. PATENT DOCUMENTS

| | | | |
|---|---|---|---|
| 990,882 | 5/1911 | Kratz | 128/305 |
| 1,195,169 | 8/1916 | Adcock | 128/305 |
| 2,934,070 | 4/1960 | Jerry | 128/354 |
| 3,100,489 | 8/1963 | Bagley | 128/354 X |
| 3,364,572 | 1/1968 | Hoppe | 128/305 X |
| 3,452,754 | 7/1969 | Stayer | 128/305 |
| 3,754,290 | 8/1973 | Nicholson | 81/43 X |
| 4,098,157 | 7/1978 | Doyle | 128/305 |
| 4,307,720 | 12/1981 | Weber, Jr. | 128/305 X |

FOREIGN PATENT DOCUMENTS 649413  1/1951  United Kingdom ................ 128/354

*Primary Examiner*—Lee S. Cohen
*Attorney, Agent, or Firm*—Daniel H. Bobis

[57] ABSTRACT

A composite tool having a preferred use as a surgical instrument has coacting resilient elongated members connected at one end to each other and movable towards and away from each other at the respective sized and shaped free ends to define a forceps or tweezers, and a scalpel blade supporting assembly slidably mounted between the coacting elongated members to move a scalpel therein from a retracted or concealed position between the coacting elongated members to an extended or cutting position, said forceps and scalpel blade supporting assembly including a locking assembly with a self-locking section for selectively, alternatively and interchangeably converting the forceps into a scalpel and vice versa wherein the forceps becomes the holder for the scalpel when the scalpel is moved from the retracted or non-cutting concealed position to the extended or cutting position, and an electrical connection on the coacting resilient elongated members to connect the composite tool to an electric circuit to permit the tool to become an electrical conductor and to be used for example as a coagulator.

10 Claims, 12 Drawing Figures

FORCEPS, SCALPEL AND BLOOD COAGULATING SURGICAL INSTRUMENT

BACKGROUND OF THE INVENTION

This invention relates generally to combination or composite tools and more particularly to a surgical instrument adapted to be selectively and interchangeably used either as a forceps or as a scalpel and adaptable for connecting the instrument to an electrical circuit for coagulating blood during surgical techniques.

The use of composite or combination tools that can be converted selectively and alternatively for more than one use are known.

In the field of medicine, surgical tools have found wide and varied usage and composite tools in which forceps or tweezers can coact with other elements for performing other functions such as piercing or cutting are known in the art as is shown by U.S. Pat. Nos. 990,882, 2,934,070 and 3,364,572.

Various surgical techniques requiring general anesthesia such as breast reduction and abdominoplasty can become so involved that several hours may be spent by the surgeon in cutting tissue and coagulating blood vessels before closing of surgical incisions can be commenced.

Since time spent under general anesthesia as will be understood by those skilled in the art is best kept to a minimum, these above mentioned operations as well as other complex operations often present problems which are highly distressing to the surgeon particularly when the patient bleeds more than usual because the cut-blot-coagulating sequence, hereinafter C-B-C, keeps repeating itself over and over again. Each C-B-C sequence requires that instruments change hands between the surgeon and his operating room nurses and assistants which causes a loss of time with each exchange cycle of these instruments. This loss of time multiplies unnoticed to the surgeon because he is busily involved in the complex details of the surgery.

The present invention seeks to provide an improved composite tool or surgical instrument operable as a forceps, a scalpel and a coagulating means selectively and alternatively and which can be utilized by a surgeon during an operation where the C-B-C sequence is frequent or for that matter in any type of surgical procedure in which it is desirable to reduce wasted instrument exchange time among the members of the surgical team conducting a given operation.

This is accomplished in the present improved surgical instrument by providing a forceps with a scalpel blade supporting assembly which is slidably mounted thereon so that the scalpel blade can be moved from a concealed position within the forceps to a cutting position in such a manner that as the scalpel blade is moved to its cutting position the scalpel blade supporting assembly simultaneously locks the respective resilient members or arms of the forceps so that the forceps is converted into a handle or holder for the scalpel blade and the tool or surgical instrument self-locks itself when the scalpel blade is in the extended or cutting position. Further, the forceps may also be provided with a connection for connecting the forceps to an electrical current generating circuit so that an electrical current can be applied through the surgical instrument by means of a foot control which the surgeon can use to actuate the electric current generating circuit and thus pass the current through the forceps for coagulating blood in the well known manner.

SUMMARY OF THE INVENTION

Thus the present invention covers an improved composite tool or surgical instrument operable selectively, alternatively and interchangeably as a forceps and as a scalpel, a scalpel blade being connected in a scalpel blade supporting assembly which is slidably mounted on the forceps and manually operable to move the scalpel blade from a retracted or concealed position in the forceps to an extended or cutting position and vice versa, and locking means is provided on the scalpel blade supporting assembly for operative association with the forceps whereby movement of the scalpel blade supporting assembly to the cutting position acts to releasably lock the forceps and to convert the same from a forceps to a handle for the scalpel blade.

The composite tool as above described including an electrical connector thereon for connecting the same into an electrical current generating circuit which can be actuated to pass an electrical current through the composite tool for coagulating blood as may be required.

Accordingly, it is an object of the present invention to provide an improved surgical instrument operable selectively and interchangeably as a forceps, as a scalpel, and additionally as a coagulator.

It is another object of the present invention to provide a composite tool comprising a forceps with means slidably mounted thereon which acts as a scalpel blade supporting assembly for moving a scalpel blade from a concealed position in the forceps to a cutting position therein and on such movement to positively self-lock the forceps and scalpel blade supporting assembly so that the forceps forms a handle for the scalpel blade and holds the scalpel blade in the extended or cutting position until released and returned to the retracted or concealed position.

Other objects and advantages of the invention will become apparent from the following detailed description of a preferred embodiment made with reference to the accompanying drawings wherein:

Figure 1:
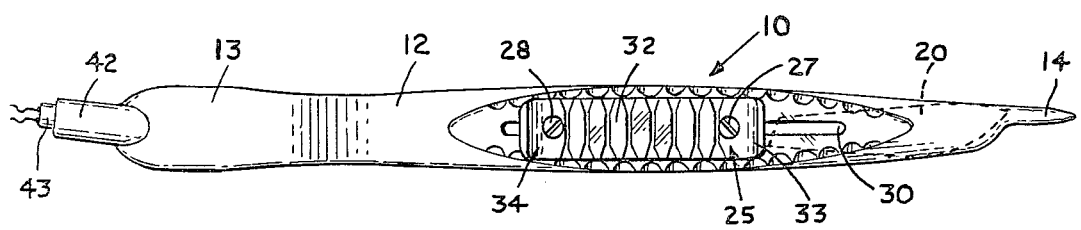
FIG. 1 is a front side elevational view of a surgical tool in accordance with the present invention with the scalpel blade in the concealed position.

Referring to the drawings a composite tool in accordance with the present invention is shown in one preferred use as a surgical instrument generally designated 10 which has coacting resilient elongated members 11 and 12 connected at one end as at 13 to each other and movable towards and away from each other at their respective sized and shaped free ends 14 and 15 to define a forceps or tweezers.

The coacting members or legs 11 and 12 will be made of materials which are inherently resilient so that when they are squeezed together the energy caused by the compression will cause the legs to expand and separate from each other when the pressure thereon is released as will be understood by those skilled in the art.

FIG. 1 shows that the respective coacting members 11 and 12 are slightly curved along their longitudinal length for reasons that will be clear from the description below and have a width in the medial section which will be slightly greater than the width of the scalpel blade generally designated 20 which is concealed between the coacting legs when it is in the retracted or concealed position as is shown by the phantomized line. This will protect the person utilizing the composite tool from being cut accidentally when the scalpel blade is in the retracted or concealed position.

Figure 2:
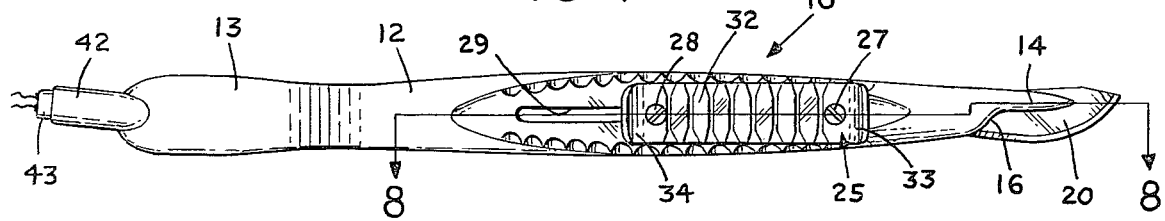
FIG. 2 is a front side elevational view of the surgical instrument shown in FIG. 1 with the scalpel blade in the cutting position.
Figure 3:
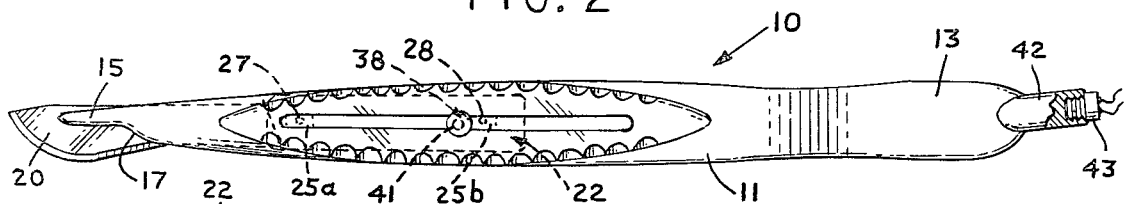
FIG. 3 is a back side elevational view of the surgical instrument shown in FIGS. 1 and 2.
Figure 4:
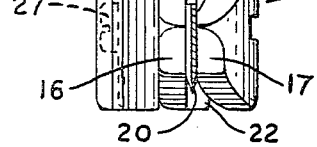
FIG. 4 is a view of the surgical instrument shown in FIGS. 1 and 2 from the scalpel end thereof.
Figure 5:
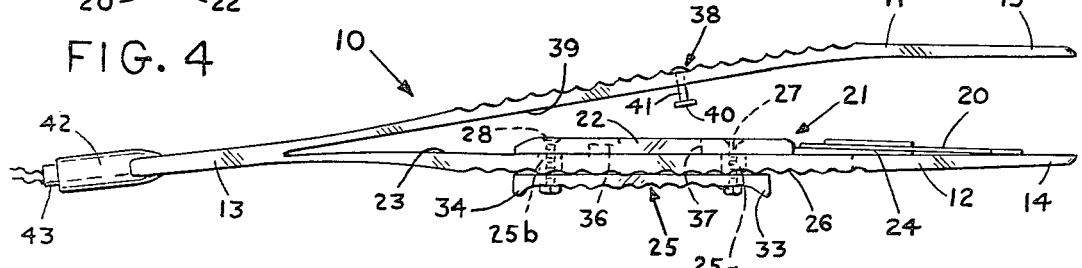
FIG. 5 is a top view of the surgical instrument shown in FIG. 1 with the scalpel blade in the concealed position.
Figure 6:
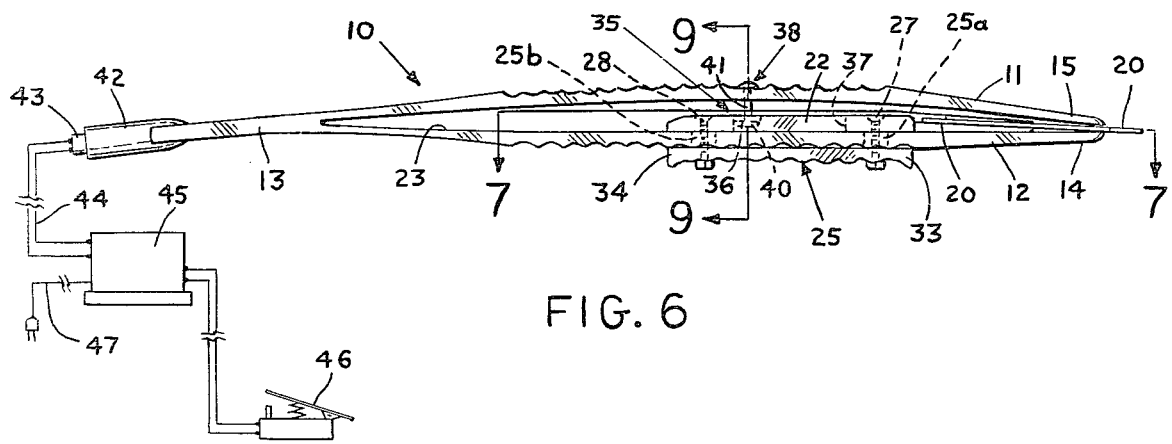
FIG. 6 is a top view of the surgical instrument shown in FIG. 2 with the scalpel blade in the cutting position and showing diagramatically the electrical circuit connected to the connector on the surgical instrument for coagulating blood.
Figure 7:
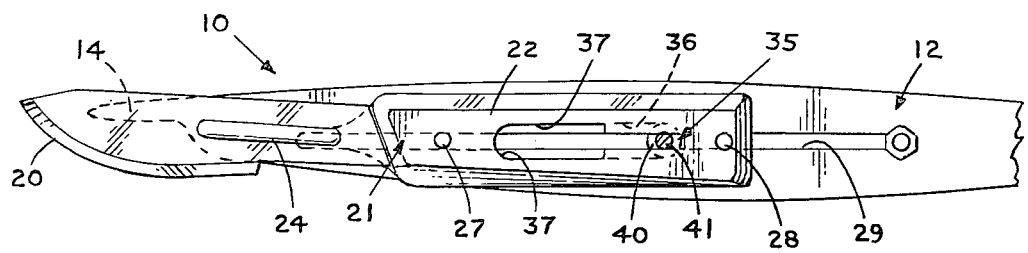
FIG. 7 is a longitudinal inside view taken on line 7—7 of FIG. 6 to show the scalpel blade holder assembly for moving the scalpel blade into and out of cutting position.
Figure 8:
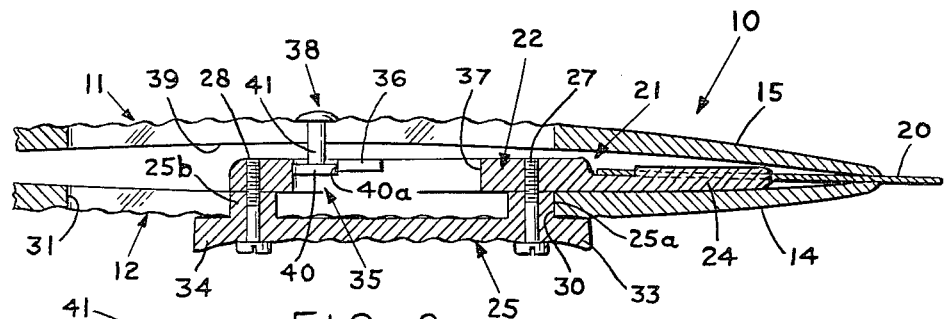
FIG. 8 is a longitudinal cross section taken on line 8—8 of FIG. 2.

The free ends of the coacting members or legs 11 and 12 will be shaped and sized so that the portions 14 and 15 generally adjacent the end can act in the conventional manner as a forceps when the coacting members 11 and 12 are squeezed together. However, inwardly of the free ends the respective coacting members or legs are cut back as at 16 and 17 to provide a substantial space. Thus, when the scalpel blade 20 is moved forward into operative extended or cutting position as shown in FIGS. 2, 4, and 6 of the drawings it will not only be supported at its upper edge by the portions 14 and 15 at the free end of the coacting legs 11 and 12 but additionally the extended end and lower cutting face of the scalpel blade 20 will be fully exposed so that the surgical instrument can now be used by the surgeon to make incisions as may be required in the course of a given operation.

In order to move the scalpel blade from the retracted or concealed position between the coacting legs or members 11 and 12 to the extended or cutting position as is shown respectively in FIGS. 2, 6, 7, and 8, the scalpel blade 20 is connected to and movable with a scalpel blade supporting assembly generally designated 21 which is slidably mounted on at least one of the coacting legs 11 or 12 as is shown in FIGS. 1 to 9 of the drawings and as now will be more fully described.

Thus, referring to FIGS. 5, 6, 7, 8, 9, 10 and 11 of the drawings scalpel blade supporting assembly 21 is shown as having a scalpel blade holder 22 which is disposed in sliding contact with the inner face 23 of the elongated member or leg 12 of the surgical instrument 10.

Scalpel blade holder 22 has a conventional blade connector 24 at the forward end which permits the scalpel blade 20 to be detachably connected to the scalpel blade holder 22 so that the scalpel blade 20 can be replaced when it becomes necessary in the conventional manner well known in the art.

In the illustrated form of the invention scalpel blade supporting assembly 21 also includes a switch plate 25 which is slidably disposed relative the outer face 26 of the elongated member or leg 12 at a point thereon in approximate alignment with the scalpel blade holder 22 so that spaced threaded members as at 27 and 28 can extend through a slotted section 29 in the elongated member or leg 12 of the forceps to fixedly connect the switch plate 25 to the scalpel blade holder 22. When the switch plate 25 is moved manually relative the elongated member or leg 12 the scalpel blade holder 22 with the scalpel blade 20 mounted thereon will move therewith both forwardly and backwardly as the case may be.

The switch plate 25 has projections as at 25a and 25b which are sized in diameter to permit the projections 25a and 25b to slide easily in the slotted section 29 as is shown in FIGS. 2, 7, 8, and 11 of the drawings. The length of the projections 25a and 25b will be approximately equal to the thickness of the elongated leg 12 to permit establishing proper frictional engagement between the scalpel blade supporting assembly 21 and the inner face 23 and outer face 26 of the elongated leg 12 for the reasons and purposes that will be clear from the following description.

In the illustrated form of the invention shown in FIGS. 1 to 11 of the drawings, the elongated member or leg 12 is slightly curved or bowed. The length of the projections 25a and 25b and adjustment of the threaded elements 27 and 28 provide means to establish adequate frictional engagement of the scalpel blade supporting assembly 21 against the inner face 23 and outer face 26 of the elongated leg 12 to insure that the scalpel blade supporting assembly 21 will be held in the retracted or concealed position and must be positively moved by indexing the switch plate 25 as by manual movement thereof to the extended or cutting position. Further, however the scalpel blade supporting assembly 21 is self-locking in the extended or cutting position to prevent the scalpel blade from accidentally retracting when in use and therefore it must also be positively released from the self-locked position in order to move the scalpel blade from the extended or cutting position to the retracted or concealed position as is now more fully also described.

Further by adjusting the length of the slotted section 29 the front closed end 30 thereof and the back closed end 31 thereof will act as stop shoulders to limit the relative forward movement and rearward movement of the scalpel blade holder 22.

Figures 9, 10, 12:
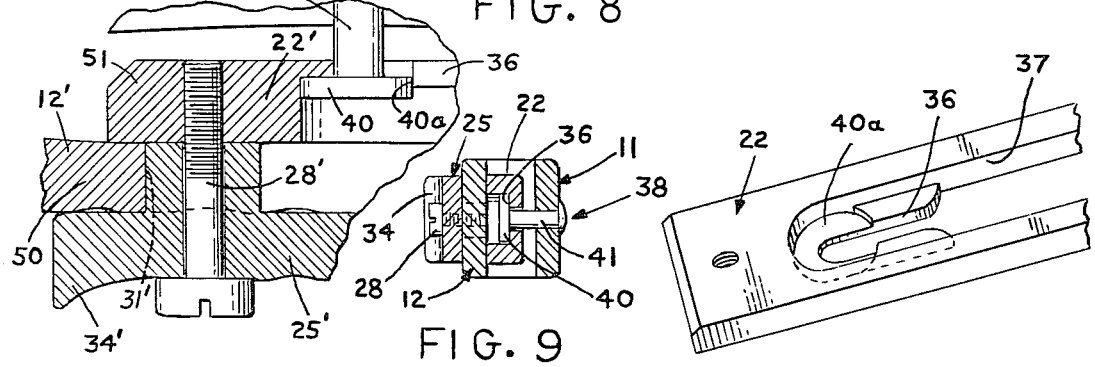
FIG. 9 is a cross section taken on line 9—9 of FIG. 6.
FIG. 10 is a fragmentary view showing the self-locking groove formed in the scalpel blade holder.
FIG. 12 is a fragmentary side elevation of an alternate way of holding the scalpel blade holder assembly in the retracted or concealed position.
Figure 11:
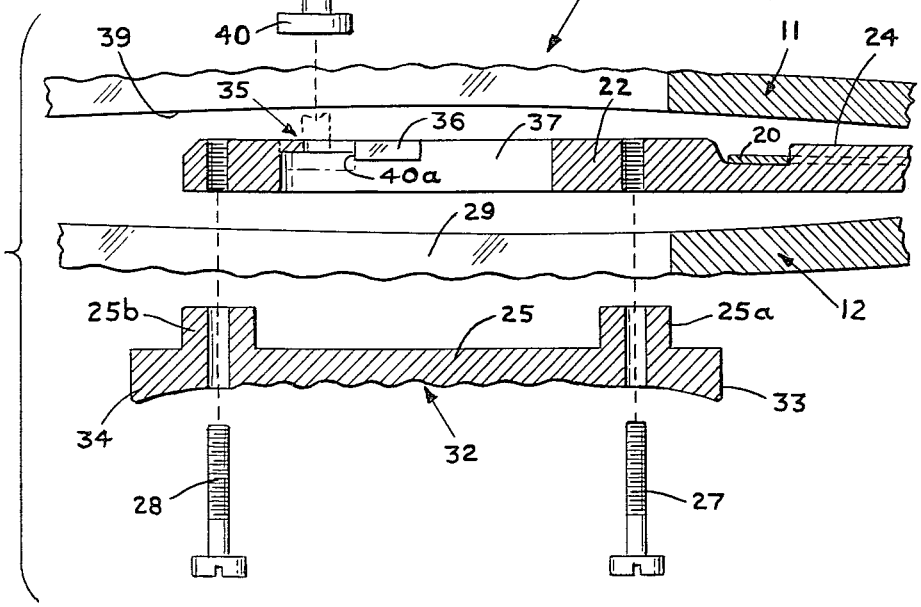
FIG. 11 is a partial explodes side view of the scalpel blade holder assembly.

In order to facilitate manual movement of the switch plate 25 it can be provided with a roughened or transversely grooved center section as at 32 and with a raised front end 33 and raised back end 34 as is clearly shown in FIGS. 2, 6 and 9 of the drawings.

To convert the forceps of the surgical instrument 10 into a handle section when the scalpel blade 20 is moved into operating or cutting position, surgical instrument 10 is provided with a latching or locking section generally designated 35 on the scalpel blade holder 22 of the scalpel blade supporting assembly which can lock and unlock the elongated members or legs 11 and 12 to each other as may be required during the use of the surgical instrument either as a forceps or as a scalpel selectively, alternatively and interchangeably.

Thus with further reference to FIGS. 2, 3, 5, 6, 7, 8, 9, 10 and 11 of the drawings the scalpel blade holder 22 is shown as having a bayonet type slot 36 formed therein which has an enlarged transverse bore 37 at the forward end thereof which transverse bore 37 is adapted for alignment with a bayonet type catch 38 connected on the inner face or wall 39 on the leg 11 opposite from the inner face 23 on the elongated member or leg 12 of the surgical instrument 10. The bayonet type catch 38 has an enlarged head 40 which has a slightly lesser diameter than the transverse bore 37.

OPERATION

Thus, when the legs 11 and 12 are brought towards each other by squeezing them together in the conventional manner, as the switch plate 25 acts to move the scalpel blade supporting assembly 21 and the scalpel blade 20 into the operating or cutting position the transverse bore 37 will be disposed to overlie and to move passed the rounded head 40 so as to permit the bayonet type slot 36 to engage the shank 41 of the bayonet type catch 38. As the scalpel blade supporting assembly 21 continues to move forward, the rounded head 40 will align with a sized self-locking groove 40a so that when the pressure being exerted against the outer faces of the elongated legs 11 and 12 is released the rounded head 40 moves into engagement with the sized self-locking groove 40a thus simultaneously locking the elongated legs 11 and 12 together so they become a handle for the now extended scalpel blade 20 and also blocking the scalpel blade supporting assembly 21 from rearward movement until the rounded head 40 is released from engagement with the self-locking groove 41 in the scalpel blade holder 22.

The resilient characteristics of the elongated members 11 and 12 and the latching or locking device 35 on the scalpel blade supporting assembly act both to hold the legs 11 and 12 together and the scalpel blade supporting assembly 21 in the extended or cutting position until such time as the surgeon utilizing the surgical instrument 10 acts to squeeze the elongated members 11 and 12 together and to manually move the switch plate 25 in a rearward direction. When the enlarged bore 37 comes into alignment with the enlarged head 40 the legs 11 and 12 can then spring away from each other as the manually exerted compressive forces are released.

In this unlocked position where the elongated members or legs 11 and 12 are separated from each other, the scalpel blade 20 can be moved to the retracted or concealed position and the surgeon can utilize the surgical instrument 10 as a forceps in the conventional manner.

Thus by manual movement of the scalpel blade supporting assembly 21 and the engagement of the latching assembly 35, the surgical instrument can be converted selectively, alternatively and interchangeably at the will of the surgeon into a forceps or a scalpel as may be necessary during the use of the surgical instrument 10.

As a further extension of the composite character of the surgical instrument 10 there is provided preferably at the connected end 13 an electrical connection 42 into which an electrical connector 43 can be connected. The electrical line 44 connects the connector 43 into a suitable electrical circuit generally designated 45 which will supply a sufficiently high current when the switch member 46 is moved from the normally open to the closed position. Current for the circuit 45 is provided from a conventional electrical outlet, not shown, into which the outlet connector 43 is inserted. The current is passed through the forceps and utilized by the surgeon to cauterize open blood vessels so as to coagulate blood at a given incision made during the operation.

The use of a forceps in combination with an electric circuit for this purpose is an old and well known expedient and hence is not more fully described herein.

FIG. 12 shows an alternate embodiment for maintaining the scalpel blade supporting assembly 21' in the retracted position. In this arrangement the elongated leg 12' is made thicker as at 59 adjacent the back stop shoulder 31'. The threaded member 28' is adjusted so that the elongated extended end 51 of the scalpel blade holder 22' and the end 34' of the switch plate 25' engage in force fit relationship with the thickened section 50 when the scalpel blade supporting assembly 21' is moved to the retracted or concealed position. Positive force must be exerted to disengage the scalpel blade supporting assembly 21' from this retracted or concealed position of the scalpel blade.

Thus an improved composite tool in the form of a preferred application thereof as a surgical instrument has been disclosed. This composite tool is of course equally applicable to any other usage where a forceps or tweezers and a cutting means can be alternatively, selectively and interchangeably used and where additionally it may be desirable to provide an electrical current.

It will be understood that the invention is not to be limited to the specific construction or arrangement of parts shown but that they may be widely modified within the invention defined by the claims.

What is claimed is:

1. A composite tool such as a surgical instrument comprising,
   a. forceps having spaced resilient elongated coacting legs,
   b. a scalpel blade supporting assembly having a scalpel blade therein slidably mounted between the coacting legs of the forceps and normally disposed so that the scalpel blade is in a retracted concealed position relative said coacting legs,
   c. said scalpel blade supporting assembly slidable relative the forceps to move the scalpel blade to and to hold the same in an extended cutting cutting position relative said coacting legs, and
   d. releasable locking means on said scalpel blade supporting assembly detachably connectible to the spaced coacting legs of the forceps to convert the forceps into a holder for the scalpel blade when the scalpel blade supporting assembly moves the scalpel blade to the cutting position.

2. In a composite tool as claimed in claim 1, including means on the scalpel blade supporting assembly for exerting frictional engagement on the associated forceps to hold the scalpel blade in the retracted concealed position.

3. In a composite tool as claimed in claim 1 wherein the releasable locking means on said scalpel blade supporting assembly includes, self-locking means to require positive force to move the scalpel blade from the extended cutting to the retracted concealed position.

4. In a composite tool as claimed in claim 1 including,
   a. means on the scalpel blade supporting assembly for exerting frictional engagement on the associated forceps to hold the scalpel blade in the retracted concealed position, and b. said releasable locking means including, a self-locking means to hold said scalpel blade supporting assembly and the scalpel blade therein in the cutting position so as to require positive force to move the scalpel blade from the cutting to the concealed position.

5. In a composite tool as claimed in claim 1 wherein,
a. the scalpel blade supporting assembly includes a scalpel blade holder, a switch plate, and means for aligning and connecting the scalpel blade holder and said switch plate to each other in assembled position on said forceps,
b. said switch plate having, sized projections thereon, and
c. threaded members extending through said sized projections in threaded engagement with the scalpel blade holder and operatively associated with the sized projections to establish frictional engagement between the scalpel blade supporting assembly and the forceps.

6. In a composite tool as claimed in claim 5 wherein,
a. the scalpel blade supporting assembly is mounted on at least one of said spaced legs of the forceps, and
b. said at least one leg being slightly bowed.

7. In a composite tool as claimed in claim 5 wherein,
a. the scalpel blade supporting assembly is mounted on at least one of said spaced legs of the forceps, and
b. said at least one leg having a thickness to cause the scalpel blade supporting assembly mounted thereon to form a force fit therewith when the scalpel blade and scalpel blade supporting assembly are in the retracted concealed position.

8. In a composite tool as claimed in claim 1 wherein said forceps is generally conductive and further includes,
a. an electrical connector on said forceps,
b. an electrical current generating means for delivering current having, means connected to said electrical connector on the forceps, and
c. a selectively operable switch in the electrical current generating means normally open and movable selectively to closed position to cause current to pass to said forceps as may be required.

9. In a composite tool as claimed in claim 1 wherein,
a. the releasable locking means so as to convert it to a holder for the scalpel blade is a stud having an enlarged head, and
b. said scalpel blade supporting assembly having a bayonet slot and a self-locking groove thereon disposed to coact with said stud and the enlarged head thereon during sliding movement of the scalpel blade to the extended cutting position.

10. In the composite tool as claimed in claim 1 including,
a. spaced stop shoulders on the forceps, and
b. said scalpel blade supporting assembly disposed on movement thereof to engage said spaced stop shoulders so as to limit the movement of the scalpel blade thereon to the concealed position and from the concealed position to the cutting position.

* * * * *